United States Patent
Roffé et al.

(10) Patent No.: US 10,667,776 B2
(45) Date of Patent: Jun. 2, 2020

(54) CLASSIFYING VIEWS OF AN ANGIOGRAPHIC MEDICAL IMAGING SYSTEM

(71) Applicant: Siemens Healthcare GmbH, Erlangen (DE)

(72) Inventors: Guillaume Roffé, Aviron (FR); Tiziano Passerini, Plainsboro, NJ (US); Puneet Sharma, Monmouth Junction, NJ (US)

(73) Assignee: Siemens Healthcare GmbH, Erlangen (DE)

( * ) Notice: Subject to any disclaimer, the term of this patent is extended or adjusted under 35 U.S.C. 154(b) by 291 days.

(21) Appl. No.: 15/670,321

(22) Filed: Aug. 7, 2017

(65) Prior Publication Data

US 2018/0042566 A1    Feb. 15, 2018

Related U.S. Application Data

(60) Provisional application No. 62/373,446, filed on Aug. 11, 2016.

(51) Int. Cl.
*A61B 6/00* (2006.01)
*G06T 7/33* (2017.01)
*G06T 7/00* (2017.01)

(52) U.S. Cl.
CPC ........... *A61B 6/504* (2013.01); *A61B 6/4441* (2013.01); *A61B 6/481* (2013.01); *A61B 6/487* (2013.01); *A61B 6/5211* (2013.01); *G06T 7/0016* (2013.01); *G06T 7/33* (2017.01); *G06T 7/97* (2017.01); *A61B 6/545* (2013.01); *G06T 7/0012* (2013.01); *G06T 2207/10016* (2013.01); *G06T 2207/10116* (2013.01); *G06T 2207/20081* (2013.01); *G06T 2207/20084* (2013.01); *G06T 2207/30101* (2013.01)

(58) Field of Classification Search
CPC ....... A61B 6/504; A61B 6/5211; A61B 6/487; A61B 6/481; A61B 6/4441; A61B 6/545; G06T 7/0016; G06T 7/33; G06T 7/97; G06T 2207/20084; G06T 2207/20081; G06T 2207/10116; G06T 2207/10016; G06T 2207/30101; G06T 7/0012
See application file for complete search history.

(56) References Cited

U.S. PATENT DOCUMENTS

| 7,822,252 B2 | 10/2010 | Bi et al. | |
|---|---|---|---|
| 8,565,859 B2 * | 10/2013 | Wang | A61B 6/00 382/128 |
| 2005/0059876 A1 | 3/2005 | Krishnan et al. | |

(Continued)

OTHER PUBLICATIONS

Wang, Fei, et al. "Automatic classification of images of an angiography sequence using modified shape context-based spatial pyramid kernels." 2011 IEEE International Symposium on Biomedical Imaging: From Nano to Macro. IEEE, 2011. (Year: 2011).*

(Continued)

*Primary Examiner* — Bobbak Safaipour

(57) ABSTRACT

Systems and methods are provided for acquiring a series of angiographic images and identifying the anatomical structures represented in the series of images using a machine learnt classifier. Additional series of images that would yield the optimal visualization of the structure of interest may be suggested.

20 Claims, 5 Drawing Sheets

(56) References Cited

U.S. PATENT DOCUMENTS

| | | |
|---|---|---|
| 2011/0052026 A1 | 3/2011 | Liao et al. |
| 2013/0345559 A1* | 12/2013 | Haemmerich ....... A61B 5/0275 |
| | | 600/431 |
| 2014/0094691 A1 | 4/2014 | Steinberg et al. |
| 2017/0221234 A1* | 8/2017 | Chen .................... G06T 11/008 |
| 2018/0028079 A1* | 2/2018 | Gurevich ............. G06K 9/6219 |
| 2019/0019579 A1* | 1/2019 | Auvray .................. A61B 6/481 |
| 2019/0159683 A1* | 5/2019 | Ma ....................... A61B 5/1073 |

OTHER PUBLICATIONS

Syeda-Mahmood, T., et al. "Automatic selection of keyframes from angiogram videos." 2010 20th International Conference on Pattern Recognition. IEEE, 2010. (Year: 2010).*

* cited by examiner

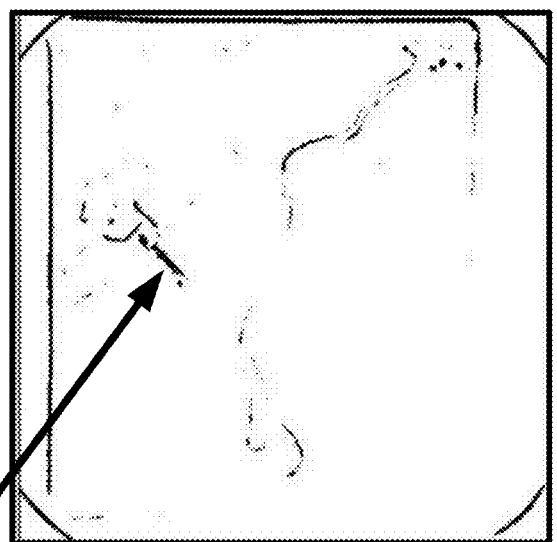
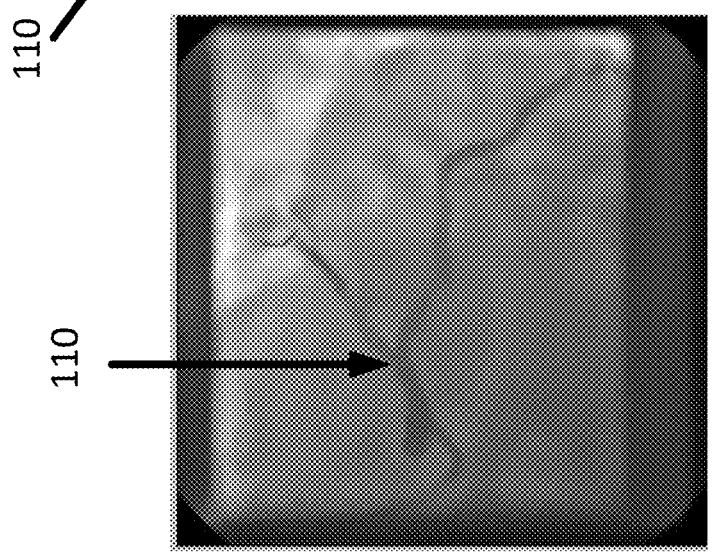
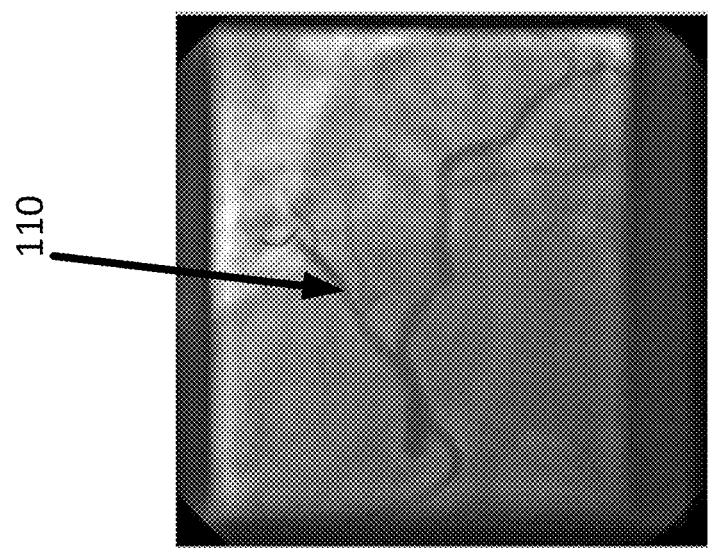

CLASSIFYING VIEWS OF AN ANGIOGRAPHIC MEDICAL IMAGING SYSTEM

CROSS REFERENCE TO RELATED APPLICATIONS

The present application claims the benefit of U.S. Provisional Application Ser. No. 62/373,446 filed Aug. 11, 2016, the disclosure of which is herein incorporated by reference in its entirety.

BACKGROUND

The present embodiments relate to classification of angiographic images.

For hospitals and medical organizations, the efficiency of medical workflows is of key importance. Each additional step or delay adds time and expense to operations. For example, in the assessment of coronary artery disease, coronary angiography may be used as the imaging modality. The detection, assessment, and treatment of coronary artery disease in the catheterization lab is manually controlled by a user, potentially resulting in an inefficient and non-reproducible workflow for each user.

One challenge in coronary angiography is the identification of the optimal views for the assessment of a disease. The correct visualization of the coronary anatomy is made difficult by the anatomical complexity of the coronary tree that may result in projections that are difficult to read and identify. Any mistake that is made may lead to delays, increased costs, or harm to a patient.

SUMMARY

By way of introduction, the preferred embodiments described below include methods and systems for acquiring a series of angiographic images and identifying the anatomical structures represented in the series of images using a machine learnt classifier. Additional series of images that would yield the optimal visualization of the structure of interest may be suggested.

In a first aspect, a method is provided for classifying a video in coronary angiography. A temporal series of angiographic images is acquired. One or more image frames are removed from the temporal series of angiographic images. A machine-learnt classifier classifies each of the remaining image frames of the temporal series of angiographic images as visualizing a first anatomical structure or a second anatomical structure. The temporal series of angiographic image frames is labeled as visualizing the first anatomical structure or the second anatomical structure based on the classifications of the remaining images. The label of the temporal series is provided to a user.

In a second aspect, a method is provided for classifying views in angiography. A temporal series of angiographic images is acquired. A deep machine-learnt classifier classifies a view of an anatomical structure in each of the images of the temporal series of angiographic images. The temporal series of angiographic images is scored based on the classifications of the view in each of the images. A second view is identified for the anatomical structure based on the score. The second view comprising scan parameters for acquiring a second set of angiographic images. The second set of angiographic images is acquired using the scan parameters.

In a third aspect, a system is provided for classifying views in angiography. The system includes a medical image scanner, a processor, and a display. The medical image scanner is configured to acquire a temporal series of angiographic images. The processor is configured to classify each of the images of the temporal set of angiographic images as visualizing an anatomical structure using a machine-learnt classifier. The processor is further configured to determine a label for the temporal series of angiographic images based on the classifications of each of the images. The display is configured to display the temporal series of angiographic images and the label.

The present invention is defined by the following claims, and nothing in this section should be taken as a limitation on those claims. Further aspects and advantages of the invention are discussed below in conjunction with the preferred embodiments and may be later claimed independently or in combination.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

FIGS. 3A, 3B, and 3C illustrate examples of detecting contrast in an image frame.

DETAILED DESCRIPTION

A series of angiographic image frames are classified based on a deep learning classifier. The classifier accepts as input, image frames of the series of angiographic frames and classifies the content of the image frames based on the image features. The classification is used to provide a label for the series of image frames. The label is provided to a user. Based on the classification and a scoring mechanism, the system may recommend a view to achieve visualization of the anatomical structure of interest.

Angiography is a minimally invasive medical test that helps physicians diagnose and treat medical conditions. Angiography uses one of three imaging technologies and, in most cases, a contrast material is injected to produce images of blood vessels in the body of a patient. Angiography may be performed using x-rays with catheters, computed tomography (CT), and/or magnetic resonance imaging (MRI). Angiography may produce a single image frame or a series of image frames captured over time. The series of image frames may be used to generate a video that provides guidance for a user. The views depicted in the angiography image frames may be influenced by the positioning of the patient and the scanner. Different angles between the patient and scanner may provide different views of the same structure or different views of different structures.

Figure 1C:
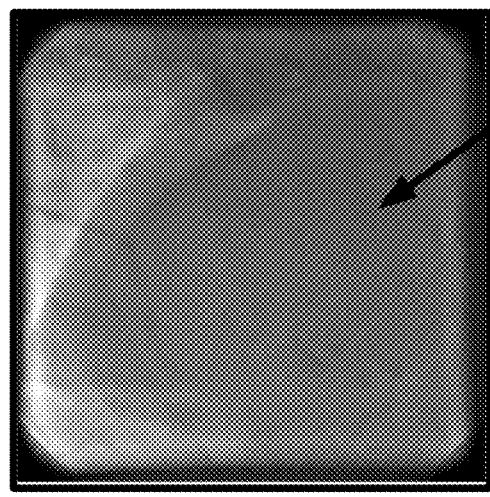
FIGS. 1A, 1B, and 1C illustrate three angiography images.
Figure 1B:
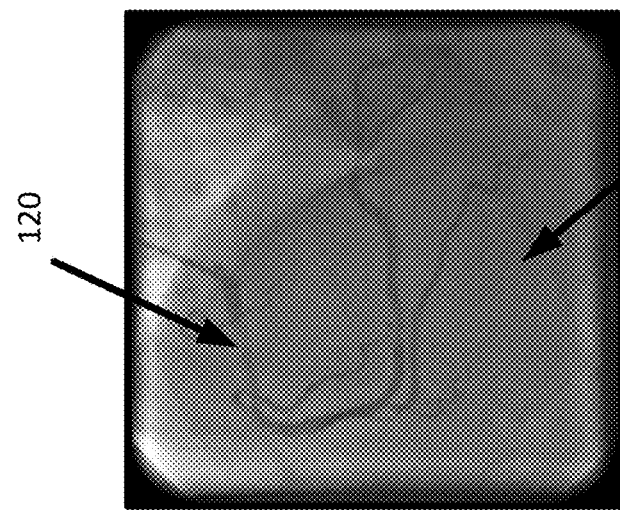
Figure 1A:
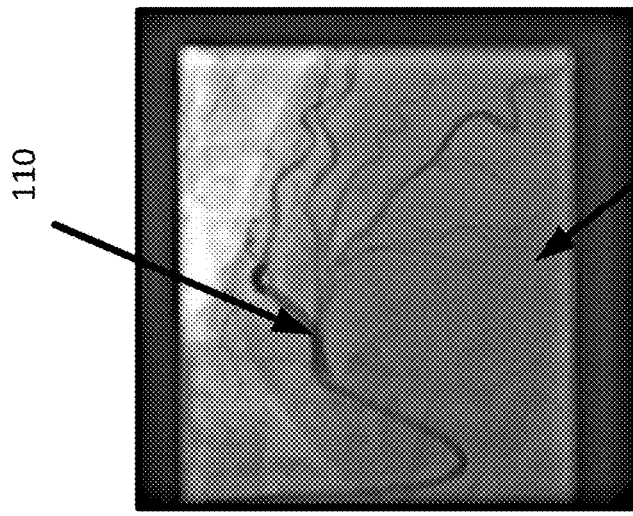

FIGS. 1A, 1B, and 1C depict three image frames produced through x-ray angiography. Each of FIGS. 1A, 1B, and 1C are captured using a medical image scanner and include a visualization (view) of a heart 130. FIGS. 1A and 1B depict scans of the heart 130 where a contrast agent has been applied. FIG. 1A depicts the left coronary artery 110.

FIG. 1B depicts the right coronary artery 120. FIG. 1C depicts an image that does not contain a view of an anatomical structure. FIG. 1C may depict an example of a scan without contrast or a scan that was not focused in the correct area. Each of the frames may be part of a series of frames that depict movement over time of the heart. To an untrained eye, determining which artery is depicted in each frame may be difficult.

During an angiography procedure, a patient is placed in the scanning apparatus. A scanning device is operated to scan the body of a patient. The images produced by the scanning device are provided to an operator. The selection of angiographic views for optimal visualization of coronary arteries may be done by the operator based on standard procedures, best practices, and/or the operator's judgement. The operator sets up the machine and selects a potential view based on his or her experience. Identification of the resulting image is based on the operator's judgment.

For example, in FIGS. 1A, 1B, and 1C, the three views include views of the left coronary artery (LCA) and right coronary artery (RCA). Which view depicts the correct structures and whether or not the view is optimal is left up to the operator. A misdiagnosis or misidentification of the structure in the view may result in an error or harm to the patient. Capturing multiple views without guidance may be inefficient and also harmful to the patient due to prolonged exposure to x-rays.

Figure 2:
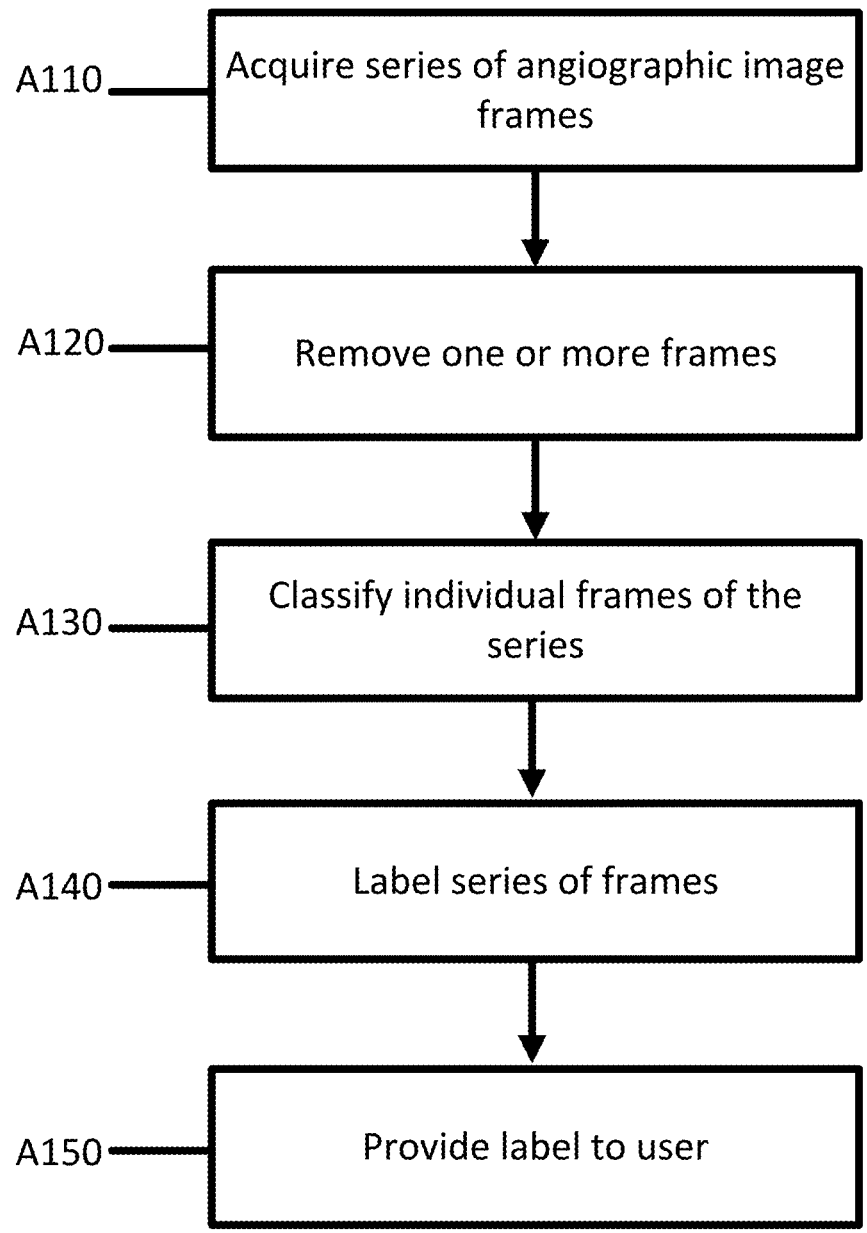
FIG. 2 illustrates one embodiment of a method for providing guidance in angiographic imaging

FIG. 2 illustrates one embodiment of a method for providing guidance in selecting a view by using a classifier to automatically classify angiographic videos scans. A video including a series of temporal image frames is captured by a medical scanning device. Machine learning is used to distinguish between right or left coronary arteries of the heart for individual image frames of the series. The series of temporal images is labeled as depicting the right or left coronary artery depending on the outcome for the classification of individual images frames. The label is presented to a user.

Figure 5:
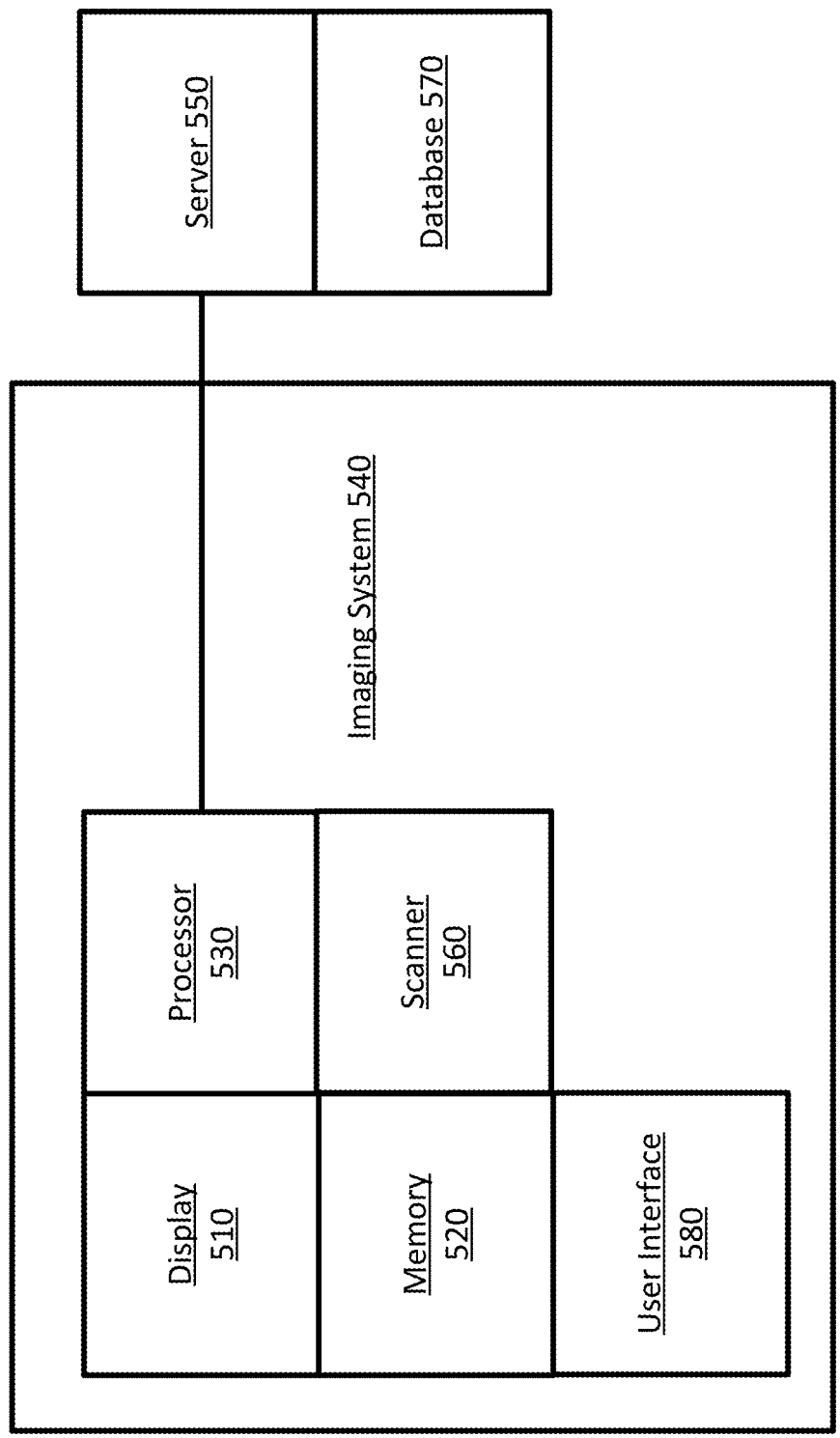
FIG. 5 is a block diagram of one embodiment of a system for providing guidance for angiographic imaging.

The acts are performed by the system of FIG. 5, other systems, a medical scanner, a workstation, a computer, and/or a server. For example, A110 is performed by a medical imaging device. Act A130 is performed by a processing component, such as the medical scanner, a workstation, or a computer. Act A120 may be skipped in certain embodiments or combined with act A130. Additional, different, or fewer acts may be provided. The acts are performed in the order shown (e.g., top to bottom) or other orders.

In act A110, a temporal series of angiographic image frames is acquired. Angiography is a medical imaging technique used to visualize the inside, or lumen, of blood vessels and organs of the body. A contrast agent may be injected into the blood vessel of a patient. The patient is scanned by a medical imaging (or scanning) device that produces an image with the contrast agent distinguished from the surrounding tissue. Multiple images taken over time (e.g. a series of frames—each image is an image frame of the series) may be combined to generate a temporal series or video of the inside of the blood vessels and/or organs of a patient. In certain embodiments, a contrast agent may not be used. As a result, the anatomical structures in the acquired images may be more difficult for an operator to manually determine. The acquired images may be presented to a user as the images are acquired or with a delay in order to perform the labeling of the series. The acquired images may be stored for later analysis in a memory or database, for example, using a Digital Imaging and Communication (DICOM) standard. In an embodiment, the acquired images may be transmitted remotely for analysis.

One of the most common angiograms performed is to visualize the blood in the coronary arteries. A catheter is used to administer a contrast agent at the desired area to be visualized. The catheter is threaded into an artery, for example, in the forearm, and the tip of the catheter is advanced through the arterial system into the coronary artery. Contrast agent is then injected. The medical imaging device generates an image of the contrast agent. Images of the distribution of the contrast agent within the blood flowing inside the coronary arteries allow visualization of the size of the artery openings. FIGS. 1A, 1B, and 1C depict three different images from three different series of such an angiogram. FIGS. 1A and 1B both show traces of the contrast agent. The contrast agent allows a viewer to distinguish between the arteries and tissues of the patient. For example, in FIGS. 1A and 1B, a user may be able to identify the LCA and RCA. In FIG. 1C, the arteries may be difficult to identify due to the lack of contrast agent.

In an embodiment, different types of medical image and corresponding medical scanners may be used to generate the angiographic images. In an embodiment, an x-ray scanner may be used to generate two-dimensional images. In one embodiment, the medical image is a computed tomography (CT) image acquired with a CT system. For CT, the raw data acquired with the detector is reconstructed into a three-dimensional representation. In another embodiment, magnetic resonance (MR) data representing a patient is acquired. MR data is acquired with an MR system. The data is acquired using a pulse sequence and coils for measuring magnetic response. For MR, the magnetic resonance data is k-space data. Fourier analysis is performed to reconstruct the data from the k-space into a three-dimensional object or image space.

At act A120, one or more of the acquired image frames are removed from the temporal set of angiographic images. The removed frames may exhibit a level of intensity below a threshold, making a determination difficult and inefficient. In an embodiment, the temporal set of angiographic images is preprocessed to eliminate any images that do not depict (or depict very poorly) an anatomical structure. In an embodiment, preprocessing includes determining the level of intensity in each of the images of the set of angiographic images. The level of intensity may directly relate the presence of the contrast agent in the patient. A high level of intensity may indicate that the contrast agent is present and easy to detect. A low level of intensity may indicate that the contract agent is not present in the image and/or the anatomical structure is difficult to detect. Vague or ambiguous anatomical structures in an image may result in poor labeling of the series as a whole. Further, initial and final frames typically contain no contrast medium (acquired before injection or after flush out). A number or percentage of image frames may be removed from the beginning of the series and/or a number or percentage of image frames may be removed from the end of the series.

In an example, for an angiogram of the coronary arteries, the anatomical structures may include the LCA or RCA. The preprocessing of the images does not distinguish between which of the two is present in the image, only that one or the other may be visualized. To detect whether or not an anatomical structure is present, different preprocessing techniques may be used.

In an embodiment, a denoising filter is applied to each image frame. An adaptive Gaussian thresholder is used to emphasize the dark areas in the image and turn the image from grayscale to a binary image. The number of black pixels in the filtered image are counted. A clustering method, for example k-nearest neighbors (KNN), is used to group the frames in dark and light images. The image frames that are in the light image group are removed or dropped from the series and further processing. Image frames that are low contrast and/or fail to depict an anatomical structure of interest may be ignored in acts A130 and A140 below. The images may be removed from future processing or visualization determination. The image frames that are removed may or may not remain part of the temporal series and may or may not be displayed to the user at act A150 below.

FIG. 3 depicts detection of contrast in image frames. FIG. 3A depicts a raw image acquired in act A110. The LCA 110 is visible, but there is a lot of noise in the image. FIG. 3B depicts a denoised image. The LCA 110 is visible in the image and the noise that dominated portions of FIG. 3A has been removed. FIG. 3C depicts a binarized image. A gaussian thresholder is used to emphasize the dark areas in the image. The resulting binarized image of FIG. 3C depicts an outline of the LCA 110. In an embodiment, more or less processing may be applied to the images. For example, a raw x-ray image may be clearer than a raw MRI image and thus require less processing. Different machines may provide different levels of quality of images. Different image processing techniques may be run in parallel to generate an image for classification below. For example, two or more different techniques may process a raw image frame. Each of the resulting processed image frames may be provided to the classifier for classification.

At act A130 of FIG. 2, each of the remaining images of the temporal set of angiographic images is classified using a machine-learnt classifier as visualizing the LCA or RCA. A classifier is used to identify the structure in an image. A supervised learning process may be used. Alternatively, an unsupervised learning process may be used. The classifier may be training using prior image frames. Prior images of the LCA and RCA with ground truth labels (i.e., image frame labeled as being of LCA) may be recorded. The contents of each image may be validated by one or more users. In certain embodiments, the prior images may be annotated with a quality score or attribute. Alternatively, a binary system of classification may be used, e.g. either LCA or RCA. In a third option, for example, an undeterminable classification may be used. For example, the classifier may be unable to classify an anatomical structure in the image frame. The classifier may then return a label "undeterminable." In an embodiment, that does not provide preprocessing in act A120, more images in the series may be unidentifiable. If the image frames are not preprocessed, the classifier may identify unknown or undeterminable frames. Additional classification schemes may be used. For example, additional labels may be used for other anatomical structures such as for the posterior descending artery, the right marginal artery, the left circumflex artery, the left marginal artery, the left anterior interventricular artery among others for a scan of a heart. In an embodiment, other arteries or blood vessels for other organs may be classified.

A classifier may use machine learning to learn to classify each of the image frames. Other methods such as statistical analysis or decision trees may be used to identify statistical similarity in the image frames by employing linear mathematical models or simple conditional logic. Data mining techniques may be used to identify structures in the images. Data mining techniques may be trained in an unsupervised or supervised manner.

For machine learning, support vector machines (SVMs, also support vector networks) may be used by the classifier to learn to classify the images. SVMs include supervised learning models with associated learning algorithms that analyze the image data used for classification and regression analysis. Given a set of training examples, each example marked as belonging to one or the other of two categories (e.g. LCA or RCA), an SVM training algorithm builds a model that assigns new examples to one category or the other. An SVM model is a representation of the examples as points in space, mapped so that the examples of the separate categories are divided by a clear gap that is as wide as possible. New examples are then mapped into that same space and predicted to belong to a category based on which side of the gap the images fall.

Alternative modeling systems may be used to learn to classify the image data, such as deep learning though neural networks or generative models. Deep machine learning may use neural networks to analyze the prior scan data. Neural networks may include a collection of interconnected processing nodes. The connections between the nodes may be dynamically weighted. Neural networks learn relationships through repeated exposure to data and adjustment of internal weights. Neural networks may capture nonlinearity and interactions among independent variables without pre-specification. Whereas traditional regression analysis requires that nonlinearities and interactions be detected and specified manually, neural networks perform the tasks automatically.

A convolutional neural network is a type of neural network. The layers in a convolutional neural network extract features from the input image. The deep learning learns features that are distinctive for classification. Convolution preserves the spatial relationship between pixels by learning image features using small squares of input data (i.e., filter kernels for convoluting with an input image are used). The convolutional neural network is composed for instance of N convolutional layers, M pooling layers, and 1 fully connected layer.

A convolutional layer is a layer of filters that compute a value for a section of the image. Additional convolutional layers may boost the accuracy of the neural network, but also take more time. Adjusting the size of the filters in the layers may further increase the accuracy. Large filters for initial layers and small filters for subsequent or at the end may increase performance. A pooling layer progressively reduces the spatial size of the representation to reduce the number of parameters and computation in the network, and to also control overfitting. The output from the convolutional and pooling layers represent high-level features of the input image. The purpose of the fully connected layer is to use values for these features for classifying the input image into various classes, such as LCA or RCA.

Other techniques may be used with the convolutional neural network including backpropagation. Backpropagation is used to calculate the gradients of the error with respect to all weights in the network and use gradient descent to update all filter values/weights and parameter values to minimize the output error.

In an embodiment, a generative model is used by the classifier. A generative model is a deep learnt model using restricted Boltzmann machines, deep belief network, neural autoregressive density estimators, auto-encoders, extensions thereof, or other deep learning approaches for generating a representation. In one embodiment, the trained deep generative model is a deep neural network with a set of j convolutional layers and k fully connected layers, each followed by a non-linear activation function, and a set of pooling layers for features reduction. Other layer arrangements may be used to classify the image data.

Training data for teaching the classifier system may be acquired from prior scans. Previously acquired image frames may be identified and scored. After a scan has finished and been analyzed by a user, the user may provide feedback on the images. Feedback may be provided for individual images or for the set as a whole where the feedback is then imputed to the individual images. Feedback may include a quality score and/or may verify that the labeling in act A140 below is correct. The training data may be updated at regular intervals. The classifier may be trained regularly or with different sets of training data until the classifier achieves an acceptable level of error.

At act A140, the temporal series of angiographic images is labeled as visualizing LCA or RCA based on the classification of the remaining images after act 120. Each of the individual frames of the temporal series is either removed or classified as LCA or RCA. In an embodiment, if more than 50% of the frames are classified as LCA, then the temporal series is classified as LCA. If more than 50% of the frames are classified as RCA then the temporal series is classified as RCA. The denominator for the calculation may be the total number of frames or number of frames that were classified as either LCA or RCA. For example, a series may contain 100 frames. 10 of the frames may be removed at act A120 described above due to not visualizing an anatomical structure. Of the 90 remaining frames, 60 may be classified at act A130 as LCA and 30 as RCA. Using the 90 remaining frames as the denominator, the temporal series is 66% LCA and as such is labeled LCA. Using the 100 total frames as the denominator, the temporal series is 60% LCA and as such labeled LCA. In another example, with 100 frames to start and 40 frames that were removed, the denominator may alter the labeling. Out of the 60 remaining frames, 45 were classified as LCA and 15 as RCA. Using the total frames as a denominator, only 45% were classified as LCA. Using the remaining frames, 75% were classified as LCA. In a scenario that only is concerned about the probability of the anatomical structure being LCA or RCA, the above examples may use the remaining frames as the denominator. However, in a scenario that is concerned with both the probability and quality of the series, the total frames may be used as a denominator. When judging the quality, in the second example given above, only 45% of the frames were classified as LCA. A user viewing such a series may not be able to gleam much information from such a series due to the low percentage of frames that visualize the LCA.

A temporal series may be scored with an optimality score for example, based on the distribution of labels among the individual frames. If the frames are mostly classified with the same label, then the series is classified with higher confidence and thus is graded with higher optimality score. If the frames are labeled with two different labels in about 50% of the cases, the grade is lower. For example, given a the number of frames labeled "LCA"; n the total number of frames; the optimality score s can be defined as: $s=((a-n/2)*2/n)^2$. Other functions may be used.

The optimality score is 1 if all frames are labeled LCA, or if none of the frames are (e.g. all are labeled RCA). The score is 0 if half the frames are labeled LCA. Alternative scoring systems may be used. An optimality score may be based on a subset of the series, for example, during an important time period of the series.

At act A150, the label of the series is provided to a user. The label may be overlaid as text on the series of image frames when displayed to a user. The label may be recorded and stored in memory or database. The label may be provided to a user by visual or auditory methods. The optimality score may similarly be provided to a user if an optimality score is calculated at act A140. In an embodiment, the series of temporal images are stored in a memory for later viewing. An operator may acquire multiple series of temporal images of a patient. The label and/or optimality score may be used to select which of the multiple series of temporal images is analyzed. Further, the label and optimality score may be used to provide guidance for the next view to be acquired.

Figure 4:
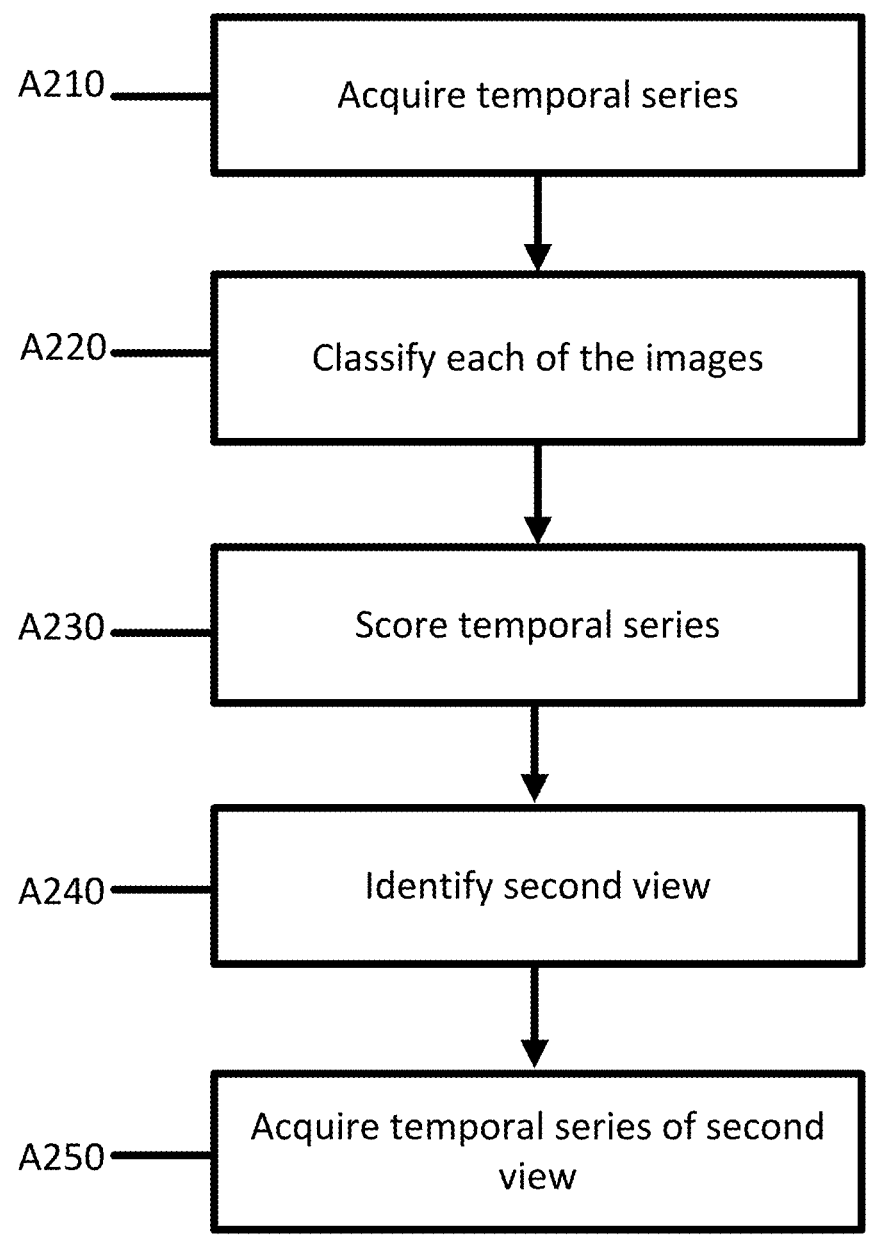
FIG. 4 illustrates one embodiment of another method for providing guidance for angiographic imaging.

FIG. 4 illustrates one embodiment of a method for providing guidance for imaging scans. A temporal series is acquired, classified, scored, and used to suggest an alternative view. The acts are performed by the system of FIG. 5, other systems, a medical scanner, a workstation, a computer, and/or a server. For example, acts A220 and A230 are performed by a processing component, such as the medical scanner, a workstation, or a computer. The acts are performed in the order shown (e.g., top to bottom) or other orders. Additional, different, or fewer acts may be used, such as performing one or the other of acts A220 and A230, but not the other.

At act A210, a temporal series of angiographic images is acquired. The angiographic images may be acquired by an X-ray scan, CT scan, or an MR scan. In an embodiment, the temporal series depicts a two-dimensional view of the interior of a patient. Different types of medical image and corresponding medical scanners may be used to generate the angiographic images. The acquired images may be two dimensional or combined to form a three-dimensional view.

In an embodiment, the positioning of a C-arm may be stored as an attribute of the temporal series of images. An angle between the C-arm and patient may determine which anatomical structure is visualized and the quality of the view. Other scan parameters may be stored. The positioning and other parameters may be used with the image data to provide training data to teach the classifier. For example, the classifier may learn to classify based on user defined labels, positioning angles, and other parameters that may be stored with the image data. The input to the classifier, for example, may be the image frame and an angle of positioning. The training data for the classifier in act A220 below may include the angiographic images and corresponding C-arm angulations as acquired during a scan.

At act A220, a view of an anatomical structure in each of the images of the set of angiographic images is classified using a deep learning classifier. Each image may be assigned a label, e.g. LCA or RCA. Each image may be rated or scored for quality or usefulness. Labels or quality scores may be recorded as individual images or series are presented to a user. The labels and or quality scores may provide feedback and training data for future analysis and updating the machine learning model, once verified as correct or not.

The classifier is any type of machine-learnt classifier that receives input parameters and outputs a classification (e.g., attributes of the image). Support vector machine, Bayesian network, a probabilistic boosting tree, neural network, sparse auto-encoding classifier, or other now known or later developed machine learning may be used. Any semi-supervised, supervised, or unsupervised learning may be used. Hierarchal, cascade, or other approaches may be used.

In one embodiment, a neural network (e.g., deep neural network) is used. Samples of image frames with user classified attributes are used to learn to classify the images. For deep learning, the classifier learns the features of the input data to extract from the training data. Alternatively, the features, at least for the input, are manually programmed, such as filtering the scan data and inputting the results of the filtering. The training relates the input data to the classification through one or more layers. One layer may relate feature values to the class. For deep-learnt networks, there may be further layers creating further abstract features from outputs of previous layers. The resulting machine-trained classifier is a matrix for inputs, weighting, and combination to output a classification and/or probability of class membership. The deep machine-trained classifier includes two or more layers relating the input to the class.

The classifier is trained using image data and/or attribute data collected from prior scans. The classifier may be trained to output a label of each of the image frames. Labels for the classifier may include attribute labels based, for example, on attributes such as clarity or quality that are user defined in the training data. The attributes may be based on one or more user's assessment of the training data. For example, the training data may be provided to a user for the user to identify the anatomical structures that is visualized and the quality of the view. Classification of the image may, for example, contain four classes: LCA good; LCA bad; RCA good; RCA bad. Additional classes or attributes may be used.

At act A230, a score for the temporal series is generated based on the classifications of the image frames determined at act A220. The score for the temporal series may be calculated as a function of the ratio of the images in the series labeled as either LCA or RCA. A temporal series may be scored with an optimality score for example, based on the distribution of labels among the individual frames. If the frames are mostly classified with the same label, then the series is classified with higher confidence and thus is graded with higher optimality score. If the frames are labeled with two different labels in about 50% of the cases, the grade is lower. For example, given a the number of frames labeled "LCA"; n the total number of frames; the optimality score s can be defined as: $s=((a-n/2)*2/n)^2$. The optimality score is 1 if all frames are labeled LCA, or if none of the frames are (e.g. all are labeled RCA). The score is 0 if half the frames are labeled LCA. Alternative scoring systems may be used. An optimality score may be based on a subset of the series, for example, during an important time period or the middle 50% of the series.

In an embodiment, an alternate classifier may be used for certain image frames. The output of the alternate classifier may be used along with the output from the first classifier to label the temporal series. If the label obtained with the alternate classifier does not agree with the label obtained with the first classifier, the optimality score may be decreased (e.g., the optimality score depends in this case on the number of frames that are classified differently by the two classifiers). An example of an alternate classifier is one detecting LCA vs RCA based on an angulation of the C-arm. Another example is a convolutional neural network with a different layer configuration.

In an embodiment, a second classifier may be used for frames (e.g. uncertain frames) that are incorrectly labeled by the first classifier. For example, if the first classifier labels 75 out of 100 frames as LCA, the other 25 that were labeled RCA may be run through the second classifier. If this second classifier detects a certain number of "uncertain frames" in the temporal series, the score of the temporal series is proportionally modified.

Other possible methods for generating an optimality score include evaluating confidence measures for neural network classifiers (such as the strength of the most activated output). Different classifiers may provide different results. For example, classifiers that contain additional layers or use larger blocks may provide more accurate results, but may also consume additional resources and take longer to provide the result. Depending on the type of scan and scan use (e.g. for immediate use or later analysis), different classifiers may be used.

At act A240, a second view of the anatomical structure is identified based on the identification and score. Optimality scores for different views may be stored in a database along with attribute data for the scan such as C-arm angulation data. Based on the anatomical structure identified in the first series, a second view may be suggested that has a higher optimality score. A second view that has a similar score may also be suggested depending on the optimality score of the initial series. For example, a user may acquire a first view at act A210. The view is classified and scored. A second view that visualizes the same anatomical structure, with potentially a better optimality score may be suggested based on prior scans and scores stored in the database. The second view may include parameters such as a C-arm angulation or other scan parameter data that was used previously.

In an embodiment, the next optimal view may be identified for instance by evaluating the C-arm angulation associated with the temporal series with the highest optimality score from previous scans (for the appropriate class). If a 3D anatomical model of the coronary tree is available (e.g. from previously acquired medical images of the patient, or from templates), then a physically-guided selection of the optimal view may be performed. The next optimal view may be identified by the appearance of the anatomical model in the given view (for which the temporal series has been acquired). The optimal positioning of the C-arm may be defined by generating a virtual angiographic series, evaluating the optimality score, and selecting the angulation that provides the highest optimality score.

At act A250, a second set of angiographic images is acquired. The second view may include scan parameters such as a C-arm angulation. The second view may be provided as an option for the user. Similar to act A210, the angiographic images may be acquired by a CT scan, an MR scan, or X-ray scan. Different types of medical imaging techniques and corresponding medical scanners may be used to generate the angiographic images. The acquired images may be two dimensional or three dimensional. The second set of angiographic images may be acquired using the same modality as the first scan. Alternatively, the second set of angiographic images may be acquired using a different modality.

FIG. 5 shows one embodiment of a system for providing guidance for angiography imaging. The system includes an imaging system 540, a server 550, and a database 570. The imaging system includes a processor 530, a memory 520, a display 550, and a scanner 560. Additional, different, or fewer components may be provided. For example, network connections or interfaces may be provided, such as for networking with a medical imaging network or data archival system. In another example, a user interface 580 is provided as part of the display 510 or imaging system 540

The processor 530, memory 510, display 510, user interface 580, and scanner 560 are part of the imaging system 540. Alternatively, the processor 530 and memory 520 are part of an archival and/or image processing system, such as associated with a medical records database workstation or server, separate from the imaging system 540. In other embodiments, the processor 530 and memory 520, are a personal computer, such as desktop or laptop, a workstation, a server, a network, or combinations thereof. The processor 530, display 510, and memory 520 may be provided without other components for acquiring data by scanning a patient.

The imaging system 540, processor 530, memory 520, display 550, user interface 580, and scanner 560 are provided at a same location. The location may be a same room, same building, or same facility. These devices are local relative to each other and are remote to the server 550. The server 550 is spaced apart by a network by being in a different facility or by being in a different city, county, state, or country. The server 550 and database 570 may be remote from the location of the imaging system 540.

The imaging system 540 is a medical diagnostic imaging system. Computed tomography (CT), x-ray, and/or magnetic resonance (MR) systems may be used. The scanner 560 may include a transmitter and includes a detector for scanning or receiving data representative of the interior of the patient.

In one embodiment, the imaging system 540 is an x-ray system. An x-ray source is connected with a gantry. A detector is also connected with a gantry opposite the x-ray source. The patient is positioned between the source and detector. The source and detector are on opposite sides of the patient and rotate and/or translate about the patient. The detected x-ray energy passing through the patient is converted, reconstructed, or transformed into data representing different spatial locations within the patient. In an embodiment, the imaging system 540 may include a portable or mobile C-arm. The C-arm includes an X-ray source and an image intensifier or flat-panel detector. The C-shaped connecting element allows movement horizontally, vertically and around the swivel axes, so that X-ray images of the patient may be produced from almost any angle. The generator emits X-rays that penetrate the patient's body. The image intensifier or detector converts the X-rays into a visible image displayed on a monitor or stored for later use.

In another embodiment, the imaging system 540 is a MR system. The MR system includes a main field magnet, such as a cryo-magnet, and gradient coils. A whole-body coil is provided for transmitting and/or receiving. Local coils may be used, such as for receiving electromagnetic energy emitted by atoms in response to pulses. Other processing components may be provided, such as for planning and generating transmit pulses for the coils based on the sequence and for receiving and processing the received k-space data. The received k-space data is converted into object or image space data with Fourier processing.

The memory 520 may be a graphics processing memory, a video random access memory, a random-access memory, system memory, cache memory, hard drive, optical media, magnetic media, flash drive, buffer, database, combinations thereof, or other now known or later developed memory device for storing data or video information. The memory 520 is part of the imaging system 540, part of a computer associated with the processor 530, part of a database, part of another system, a picture archival memory, or a standalone device.

The memory 520 stores medical imaging data representing the patient, machine-learnt classifiers (e.g., one or more matrices), graphical or display setting, and/or images. The memory 520 may store data during processing for application and/or may store training data (e.g., images and attributes).

The memory 84 or other memory is alternatively or additionally a non-transitory computer readable storage medium storing data representing instructions executable by the programmed processor 530 for classification of the scan data. The instructions for implementing the processes, methods and/or techniques discussed herein are provided on non-transitory computer-readable storage media or memories, such as a cache, buffer, RAM, removable media, hard drive, or other computer readable storage media. Non-transitory computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code, and the like, operating alone, or in combination. Likewise, processing strategies may include multiprocessing, multitasking, parallel processing, and the like.

In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU, or system.

The processor 530 is a general processor, central processing unit, control processor, graphics processor, digital signal processor, three-dimensional rendering processor, image processor, application specific integrated circuit, field programmable gate array, digital circuit, analog circuit, combinations thereof, or other now known or later developed device for classification of an image frame using a machine learnt classifier. The processor 530 is a single device or multiple devices operating in serial, parallel, or separately. The processor 530 may be a main processor of a computer, such as a laptop or desktop computer, or may be a processor for handling some tasks in a larger system, such as in the imaging system 530. The processor 530 is configured by instructions, design, hardware, and/or software to perform the acts discussed herein.

The processor 530 and/or server 550 are configured to perform the acts discussed above for labeling of the temporal series of images. The processor 530 and/or server 550 are configured to provide guidance for labeling and/or scoring a temporal series of images. The processor 530 and/or server 550 are configured to identify anatomical structures in frames of a series of frames with a machine-trained model using statistical or machine learning processes. The processor 530 and/or server 550 may be configured to classify the frames using a convolutional neural network. One or more convolutional neural networks may be used for classification. For example, three different convolutional networks trained with different training data may be used to classify an image frame as either LCA or RCA. The classification may be determined depending on which of LCA or RCA the majority of networks classify the image frame.

The model may be trained based on prior imaging data and attributes (ground truth) stored in the database 570 or memory 520. The processor 530 and memory 520 may store individual frames, series of frames, and attributes of the image frames for the imaging system 540. The server 550 and/or database 570 may store image frames, series of images frames, and attributes of the image frames from one or more imaging systems 540. The model may be used to generate labels or scores on the display 510 of the image scanner 560.

The processor 530 and/or server 550 is configured to provide labels and scores to the display 510 or to the memory 520. The processor 530 and/or server 550 may be configured to generate a user interface for selections of scan parameters.

The display 510 is a monitor, LCD, projector, plasma display, CRT, printer, or other now known or later developed devise for outputting visual information. The display 510 receives images, graphics, text, quantities, or other information from the processor 530, memory 520, imaging system 540, and/or server 550. The display 510 is configured to provide images and labels to a user.

The user interface 580 may be configured to receive one or more selections from a user. The user interface 580 may include an input device such as one or more buttons, a keypad, a keyboard, a mouse, a stylus pen, a trackball, a rocker switch, a touch pad, a voice recognition circuit, or other device or component for inputting data. The user interface 580 and the display 510 may be combined as a touch screen that may be capacitive or resistive.

The server 550 connects to the imaging system 540 via a network. The network is a local area, wide area, enterprise, another network, or combinations thereof. In one embodiment, the network is, at least in part, the Internet. Using TCP/IP communications, the network provides for communication between the processor 530 and the server 550. Any format for communications may be used. In other embodiments, dedicated or direct communication is used.

The server 530 is a processor or group of processors. More than one server 530 may be provided. The server 530 is configured by hardware and/or software. In one embodiment, the server 530 performs machine learning with training data in the database 570. The server 530 may acquire and the database 570 may store data from multiple scanning machines.

The database 570 is a memory, such as a bank of memories, for storing training data, such as images and respective parameters. Weights or values of images or attributes of the model and/or classifier are stored in the database 570 and/or the memory 520.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

We claim:

1. A method for classifying a video in coronary angiography, the method comprising:
    acquiring a temporal series of angiographic image frames;
    removing one or more angiographic image frames from the temporal series of angiographic image frames;
    classifying by a machine-learnt classifier each of the remaining angiographic image frames of the temporal series of angiographic image frames as visualizing a first anatomical structure or a second anatomical structure;
    labeling the temporal series of angiographic image frames as visualizing the first anatomical structure or the second anatomical structure based on the classifications of the remaining images; and
    providing the label of the temporal series of angiographic image frames to a user.

2. The method of claim 1, wherein the first anatomical structure is a left coronary artery and the second anatomical structure is a right coronary artery.

3. The method of claim 1, wherein acquiring the temporal series of angiographic image frames is performed by an x-ray imaging device.

4. The method of claim 1, wherein the one or more angiographic image frames are removed based on a contrast level.

5. The method of claim 4, wherein removing comprises:
    denoising an image frame of the angiographic image frames;
    generating a binary image of the denoised image frame; and
    removing the binary denoised image frame when a contrast level does not reach a predefined threshold.

6. The method of claim 1, wherein removing comprises:
    removing a first percentage of angiographic image frames from a start of the temporal series and a second percentage of angiographic image frames from an end of the temporal series.

7. The method of claim 1, wherein classifying by a machine learnt classifier comprises:
    training a convolutional neural network with training data comprising labeled prior image frames;
    inputting each of the remaining images frames into the convolutional neural network; and
    returning a classification from the convolutional neural network.

8. The method of claim 1, wherein labeling comprises:
    comparing a number of angiographic image frames classified as the first anatomical structure versus the second anatomical structure; and
    selecting the first anatomical structure or the second anatomical structure based on the comparison.

9. The method of claim 1, further comprising:
    generating the optimality score for the temporal series of angiographic image frames as a function of:

$s=((a-n/2)*2/n)2$ wherein:

(a)=a number of angiographic frames classified as the first anatomical structure;
    (n)=a total number of angiographic frames;
    (s)=the optimality score; and
    providing the optimality score to the user.

10. A method for classifying views in angiography, the method comprising:
    acquiring a temporal series of angiographic images;
    classifying, using a deep machine-learnt classifier, a view of an anatomical structure in each of the angiographic images of the temporal series of angiographic images;
    scoring the temporal series of angiographic images based on the classifications of the view in each of the angiographic images;
    identifying, based on the score, a second view of the anatomical structure, wherein the second view comprises one or more scan parameters for acquiring the second view; and
    acquiring a second set of angiographic images with the one or more scan parameters.

11. The method of claim 10, wherein the view is classified as either a view of a left coronary artery or a view of a right coronary artery.

12. The method of claim 11, wherein scoring comprises:
    generating the score for the temporal series as a function of:

$s=((a-n/2)*2/n)2$ wherein:

(a)=a number of angiographic images classified as the view of the left coronary artery;

(n)=a total number of angiographic images; and
(s)=the score.

13. The method of claim 10, further comprising:
removing, prior to classifying, one or more angiographic images from the temporal series of angiographic images as a function of a contrast level in the one or more angiographic images.

14. The method of claim 10, further comprising:
identifying, when acquiring the temporal series, an angle of a C-arm; wherein identifying the second view is further based on the angle.

15. A system for classifying views in angiography, the system comprising:
a medical image scanner configured to acquire a temporal series of angiographic images;
a processor configured to classify each image of the temporal series of angiographic images as visualizing an anatomical structure using a machine-learnt classifier, the processor further configured to determine a label for the temporal series of angiographic images based on the classifications of each of the images; and
a display configured to display the temporal series of angiographic images and the label.

16. The system of claim 15, wherein each of the images are classified as either a view of a left coronary artery or a view of a right coronary artery.

17. The system of claim 15, wherein the processor is configured to classify each of the images using a convolutional neural network.

18. The system of claim 17, wherein the convolutional neural network is trained using image data and classification data from prior labeled images.

19. The system of claim 17, wherein the processor is configured to classify each of the images using two or more convolutional neural networks.

20. The system of claim 15, wherein the processor is further configured to calculate an optimality score for the temporal series based on the classifications.

* * * * *